United States Patent [19]

Brunty

[11] Patent Number: 5,222,733
[45] Date of Patent: Jun. 29, 1993

[54] THROWING ARM TRAINING DEVICE

[76] Inventor: Steven H. Brunty, Rte. 4, Box 3, Chesapeake, Ohio 45619

[21] Appl. No.: 717,325

[22] Filed: Jun. 18, 1991

[51] Int. Cl.⁵ .................................. A63B 69/00
[52] U.S. Cl. ..................... 273/55 R; 273/189 R; 273/29 A; 273/26 C; 273/54 B
[58] Field of Search ............... 273/55 R, 29 A, 189 A, 273/26 C, 54 B, 26 D; 128/881, 877, 87 R, DIG. 6, 77, 88, 80 R, 80 F

[56] References Cited

U.S. PATENT DOCUMENTS

| | | | |
|---|---|---|---|
| 4,088,130 | 5/1978 | Applegate | 128/80 F |
| 4,191,373 | 3/1980 | Lancoletti | 128/77 |
| 4,254,953 | 3/1981 | Marchetti et al. | 128/77 |
| 4,372,298 | 2/1983 | Lerman | 128/88 |
| 4,489,716 | 12/1984 | Blackwood | 128/77 |
| 4,493,316 | 1/1985 | Reed et al. | 128/88 |
| 4,605,227 | 8/1986 | Hurd | 273/189 A |
| 4,633,867 | 1/1987 | Klausek et al. | 128/88 |
| 4,657,000 | 4/1987 | Hepburn | 128/88 |
| 4,726,316 | 2/1988 | Farley | 128/80 B |
| 4,732,143 | 3/1988 | Kawasek et al. | 128/88 |
| 4,884,561 | 12/1989 | Letson, Sr. | 128/77 |
| 4,984,789 | 1/1991 | Socci | 273/26 C |
| 5,062,858 | 11/1991 | Broeck et al. | 128/80 F |

Primary Examiner—Theatrice Brown
Attorney, Agent, or Firm—Richard C. Litman

[57] ABSTRACT

A throwing arm training device is attached to a user's arm to limit the flexion angle of the throwing arm to a maximum angle of 90 degrees and also the angle of extension to a desired minimum angle less than 90 degrees, thereby, encouraging maximum use of the latissimus dorsi muscle while discouraging sidearm throwing. The device comprises an upper arm and a forearm cuff having bars extending therefrom pivotally connected in the vicinity of the elbow by pivot screws mounted on a plate and connected to a limit plate having two arcuate slots centered on the pivot screws. Limit screws are slidably and lockably mounted in the slots to engage and limit the pivoting of the bars, and therefore of the cuffs. The cuffs are attached to the arms by straps having VELCRO or hook fasteners and loop, and include cushioning liners therein. The preferred materials for forming the straps include polypropylene, polyethylene, and copolymers of polypropylene and polyethylene. The device may be used by football quarterbacks and baseball pitcher to teach them the proper way to throw by maximizing shoulder use or movement in the throwing motion which results in an increase in the distance thrown.

4 Claims, 2 Drawing Sheets

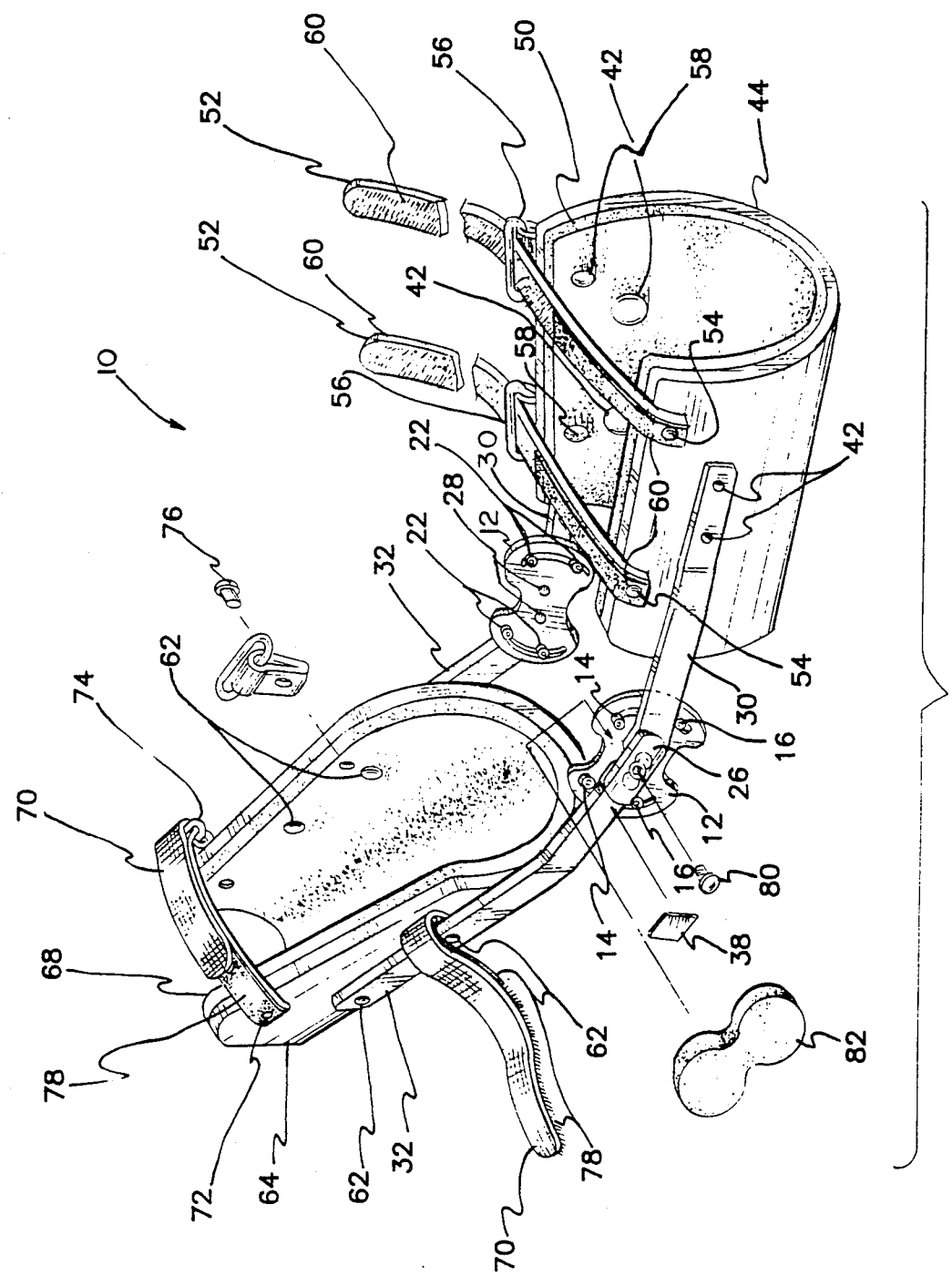

THROWING ARM TRAINING DEVICE

FIELD OF THE INVENTION

This invention relates to a throwing arm training device used to teach individuals how to throw a football or baseball properly using the correct arm and elbow action.

Football quarterbacks and baseball pitchers have all too often suffered injury to their throwing arms because they did not use the correct arm and elbow action when throwing the football or baseball. The training device of this invention will help correct this problem.

The first major function of the throwing arm training device is to restrict the passer from throwing with the arm flexed inward toward the ear past a 90 degree angle mark shown on the training device. This automatically enables the thrower to maximize shoulder use or movement in the throwing motion which results in an increase in distance thrown. The major concern is that many throwers release the ball too close to the ear (inward past the 90 degree angle), resulting in increased rotation or spin on the ball and a decrease in the distance the ball is thrown.

The second major function of the throwing arm training device is that it also restricts the passer or pitcher from releasing a football or baseball with an overextended or fully extended arm both of which are better known as the "sidearm" method. The adverse effects of the sidearm method include poor accuracy, lack of distance, and added stress placed on the muscles of both the arm and shoulder.

Both angles on the throwing arm training device are adjustable. However, the recommended adjustment limiting the flexion of the arm should be set at the 90 degree angle. The angle of coach might lock the extension adjustment at the 80 degree angle and have the subject practice throwing with the throwing arm training device on a daily basis, so that the subject will learn to effectively release the ball between the 80 degree and 90 degree angle. When the thrower and/or his or her coach decides that he or she is now comfortable with the newly formed throwing motion, the extension angle can be gradually let out or decreased over a period of time until the thrower can perform the proper throwing motion without the extension restriction. At that time, the device can be removed from the arm and a new improved throwing motion should have evolved. Now the thrower will be able to throw a football or baseball using the proper technique without the aid of the throwing arm training device.

DESCRIPTION OF RELATED PRIOR ART

Arm control devices for both behavior modification and training are well known in the prior art. U.S. Pat. No. 1,722,601 issued Aug. 12, 1930, to Berman S. Dunham discloses a thumb-sucking preventing device comprising a pair of sleeves or cuffs mountable on an arm above and below the elbow, respectively, said pair of sleeves or cuffs being pivotally connected in the vicinity of the elbow by two rotatable plates, the pivotal movement being limited by a pin and slot connection.

U.S. Pat. No. 3,074,723 issued Jan. 22, 1963, to Clement Esty discloses a golfing practice aid which comprises a sleeve or cuff which is mounted on a golfer's forearm and elbow of his leading arm to remind the golfer to keep his or her leading arm straight during the course of his or her backswing.

U.S. Pat. No. 3,439,673 issued Apr. 22, 1969, to Carl A. Sprecher discloses an elbow immobilizer for use on male and female patients to facilitate intravenous administration of food, blood, or other fluids, comprising a pair of elongated support members of sufficient length to prevent a person from bending .p180his arm, said support members being attached to the arm by a pair of straps above and below the elbow, and a third intermediate strap at the elbow.

U.S. Pat. No. 4,875,677 issued Oct. 24, 1989, to Albert G. Tetreault discloses a training aid for baseball hitters to assist in keeping a batter's lead arm flexed in a proper hitting stance, comprising a first sleeve or cuff attached to the batter's upper arm, and one or more elastic straps connected between the two cuffs.

U.S. Pat. No. 4,984,789 issued Jan. 15, 1991, to Roger D. Socci, discloses a device to help teach and train baseball pitchers to use the correct arm and elbow action when pitching a baseball, comprising an arm elevator harness which fits around the pitchers body, and an arm and elbow elevator guide which is attached to the shoulder harness and guides the pitcher's pitching arm in the right position.

SUMMARY AND OBJECT OF THE INVENTION

Not found in the prior art is a throwing arm training device wherein the flexion of the arm can be set at a 90 degree angle and the angle of extension can be varied to allow a range of extension between approximately 60 degrees and 90 degrees, depending on the severity of the sidearm problem.

It is an object of this invention to provide a throwing arm training device for football quarterbacks and baseball pitchers which avoids the defects of prior art training devices.

It is a further object of this invention to provide a throwing arm training device which adjustably limits the flexion angle and the extension angle of a throwing arm.

The throwing arm training device comprises a U-shaped sleeve or cuff for the upper arm and a U-shaped sleeve or cuff for the forearm. The cuffs may be formed of a relatively stiff plastic material such as polypropylene, a less rigid plastic material such as polyethylene, or a copolymer of polypropylene and polyethylene.

Provided within the cuffs is a liner formed of any conventional cushioning material. The cuffs are joined together on either side by a pair of bars, each pair having mating gear teeth at one end held in an engageable position by pivots mounted on a pivot support plate which in turn is connected to a metal limit guide and support plate by the pivots. The limit devices comprises screws and nuts adjustably mounted in slots provided in the limit guide and support plate. The limit screws may be tightened or loosened by means of an allen wrench. By adjusting the limit screws, the angle of flexion, preferably 90 degrees, and the angle of the ascension between 60 degrees and 90 degrees may be set. If found to be desirable, a screw may be added to the pivot plate to provide a sturdier and stronger connection. The cuffs are attached to and held onto a thrower's arm by means of flexible straps having VELCRO or hook and loop fastening means, the straps being passed through cooperating loops.

A foam rubber cushion may be provided on the inner surface of the limit guide and support plate to protect the elbow from chaffing, as shown in FIG. 3.

Other objects, features, and advantages of this invention will become apparent from the following detailed description and the appended claims, reference being had to the accompanying drawings forming a part of the specification, wherein like reference numerals designate corresponding parts of the several views.

BRIEF DESCRIPTION OF DRAWINGS

FIG. 3 is an exploded perspective view of the throwing arm training device showing how the several components cooperate and/or coact.

DETAILED DESCRIPTION OF THE PREFERRED EMBODIMENT

Before explaining in detail the present invention, it is to be understood that the invention is not limited in its application to the details of construction and arrangement of parts illustrated in the accompanying drawing, since the invention is capable of other embodiments and of being practiced or carried out in various ways. Also, it is to be understood that the phraseology and terminology employed herein is for the purpose of description and not limitation.

Figure 1:
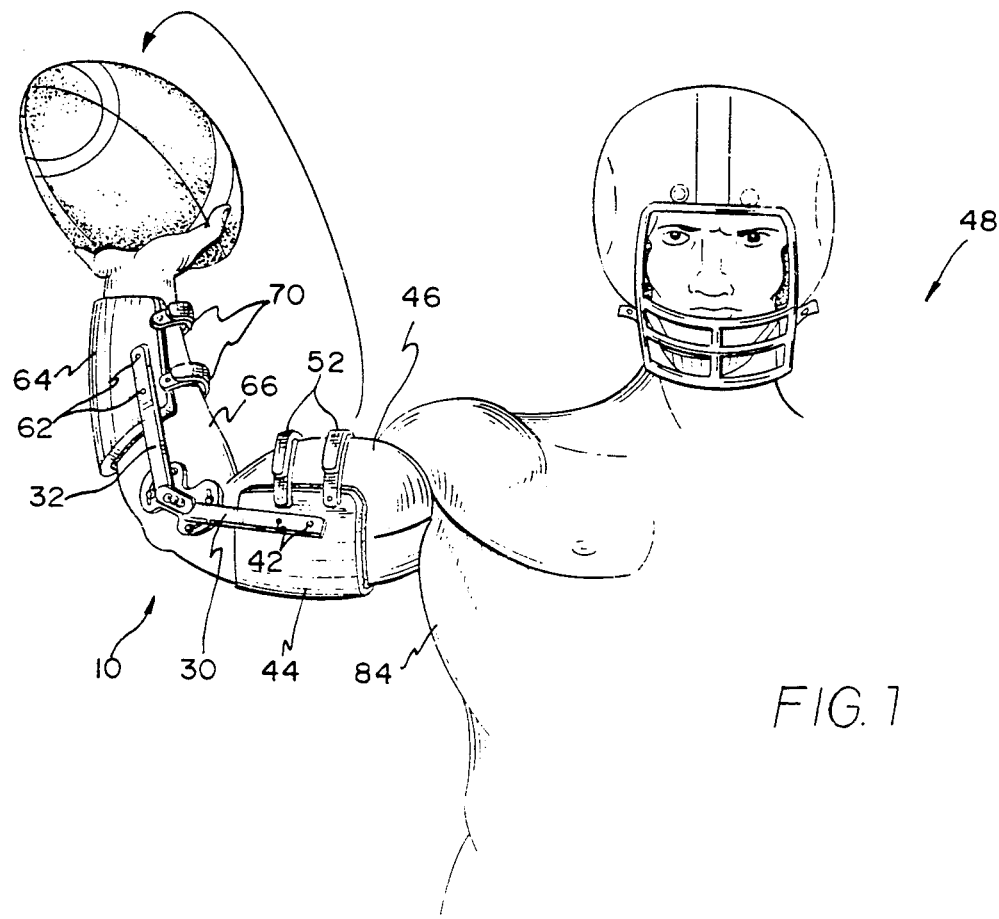
FIG. 1 is perspective view showing the throwing arm training device in use.
Figure 2:
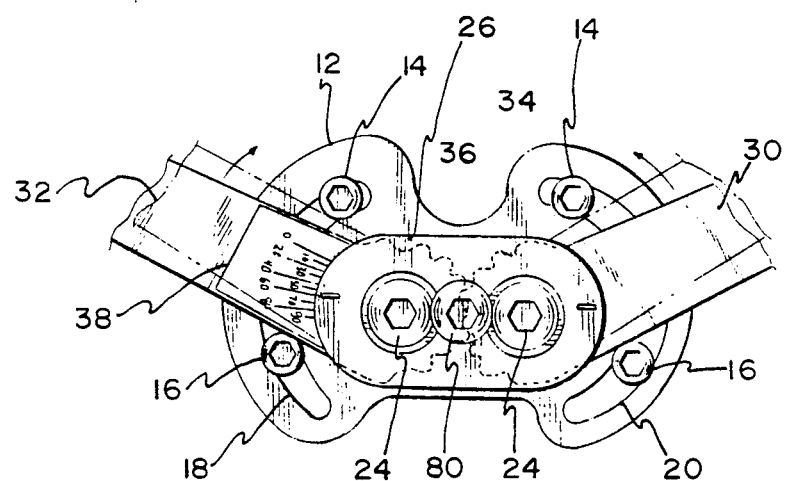
FIG. 2 is a side view showing the pivoting and limiting devices of the throwing arm training device.

FIG. 1 is a perspective view showing the throwing arm training device 10 in use. As shown in FIG. 2, the limit guide and support plate 12 limits the flexion of the forearm to 90 degrees by the placement of upper limit screws 14. Upper limit screws 14 and lower limit screws 16 are slidably adjustable along arcuate slots 18 and 20 and are locked in position by means of nuts 22. The radial centers of arcuate slots 18 and 20 are respectively located at the axis of left and right pivot screws 24.

Limit guide and support plate 12 also supports left and right pivot screws 24 which pass through openings (not shown) in pivot support plate 26 and which are screwed into threaded holes 28 in limit guide and support plate 12.

Pivotally mounted on pivot screws 24 between limit guide and support plate 12 and pivot support plate 26 are a first bar 30 and a second bar 32 having cooperating gear teeth 34 and 36. Because of the cooperating gear teeth rotation of one bar 30 or 32 about its pivot screw 24, will cause a corresponding equal and opposite rotation of the other bar 32 or 30 about its pivot screw 24, the degree of rotation being limited by upper and lower limit screws 14 and 16. Attached to second bar 32 is a scale 38 which, by cooperating with mark 40, identifies the degree of rotation of bars 30 and 32. Bar 30 is connected by rivets 42 to a U-shaped sleeve or cuff 44 configured to fit the upper arm 46 of the user 48. Cuff 44 includes a liner 50, straps 52 attached to cuff 44 by rivets 54, and loops 56 attached to cuff 44 by rivets 58. Straps 52 include VELCRO or hook and loop fastening means 60 whereby cuff 44 may be secured to upper arm 46 as shown in FIG. 1.

Bar 32 is attached by rivets 62 to U-shaped sleeve or cuff 64 configured to fit forearm 66 of user 48. Cuff 64 includes a liner 68, straps 70 attached by rivets 72 to cuff 64, and loops 74 attached to cuff 64 by rivets 76. Straps 70 include VELCRO or hook and loop fastening means 78 whereby cuff 64 may be secured to forearm 66 as shown in FIG. 1.

Elements 12, 14, 16, 18, 20, 22, 24, 26, 28, 30, 32, 34, 36, 38, 40 and 42 located along the inner side of the arm 46, 66 in FIGS. 1, 2 and 3 are duplicated on the outer side of the arm as shown in FIG. 3. As shown in FIGS. 2 and 3, a screw 80 may be added to pivot support plate 26, the head of screw 80 bearing on pivot screws 24 to provide stability therefor. In the event that limit guide and support plates 12 and nuts 22 carried by plates 12 rub against the user's elbow, a piece of sponge rubber 82 may be glued to the inner side of plates 12.

Plates 12 and 26 and bars 30 and 32 are formed of metal, such as aluminum or steel. Cuffs 44 and 64 are formed of plastic material which is fairly rigid, such as polypropylene. As an alternative, softer cuffs may be formed of polyethylene or a copolymer of polypropylene and polyethylene. In the preferred embodiment, the plastic material is approximately ⅛ inch thick. The liner is 50, 68 is formed of any conventional cushioning material. The thickness of the liner 50, 68 can vary in 1/16 increments, from ⅛ inch to ¾ inch. Because of the variance in arm sizes, it is contemplated that the cuffs 44, 64 will be made in at least three different sizes.

In use, upper limit screws 14 may be set at 90 degrees in slots 18 and 20, and if desired, such a setting may be considered as being permanent. This setting restricts the passer from throwing with the arm flexed inward towards the ear past the 90 degree angle mark shown, which forces the thrower to maximize the use of rotation of the shoulder during the throwing motion taking away from the stress on the elbow while at the same time the latissimus dorsi muscle (84, FIG. 1) plays a major role in powering the throw.

Lower limit screws 16 determine the angle of extension, which is adjusted according to the severity of the sidearm problem. As set in FIG. 2, the arm may extend over a range of 30 degrees, from 90 degrees to 60 degrees. Ideally, the throwing motion ends with an exaggerated snapping of the wrist. During a training period, lower limit screws 16 may be set at any position desired by the thrower and/or his or her coach.

While it will be apparent that the preferred embodiment of the invention herein disclosed is well calculated to fulfill the objects above-stated, it will be appreciated that the invention is susceptible to modification, variation and change without departing from the proper scope or fair meaning of the subjoined claims.

I claim:

1. A throwing arm training device comprising:
   U-shaped upper arm and fore arm cuffs, each cuff being plastic material and having a cushioning liner therein, each of said cuffs having strap means for attaching said cuffs to the throwing arm of a user;
   pivot means connected to and intermediate said upper arm and fore arm cuffs for allowing said cuffs to be pivoted relative to each other, said pivot means being worn on each side of a user's elbow when in use;
   an elongated bar member on each side of each cuff, each bar member having one of its ends attached to a cuff and its other end having a plurality of gear teeth and being attached to said pivot means adjacent its other end such that its other end is engaged with gear teeth on another of said bar members; said pivot means including a limit guide and a support plate connected to each said bar member by a pivot screw; each of said bar members being sandwiched between a pair of said limit guides and support plates, a said support plate and limit guide being on each side of said device, each of said limit guides having a pair of spaced apart arcuate slots therein each of said slots having a pair of adjustable and backable limit screws therein, each of said screws being placed on opposite sides of a bar member for engagement therewith and being adjustable along a said slot thereby limiting arm flexion angle and extension angle when worn by a user, the limit of said flexion angle being set at 90 degrees when said bar members engage a pair of limit screws and said extension angle being between 60 degrees and 90 degrees when said bar members engage another pair of said limit screws;

arm cushion means attached to each said limit guide for protection of an arm of a user;

said strap means having engageable hook and loop fasteners for attaching said device to the throwing arm of a user;

means defining a graduated scale on said support plate for indicating said flexion and extension angles of said cuffs relative to each other.

2. A throwing arm training device comprising:

U-shaped upper arm cuff means including cushioning liner means on an inner surface thereof, strap means having fastening means thereon for fastening said U-shaped upper arm cuff means to a user's upper arm, and first bar means connected to and extending from each side of said U-shaped upper arm means;

a separate U-shaped forearm cuff means including cushioning liner means on an inner surface thereof, strap means having fastening means thereon for fastening said U-shaped forearm cuff means to said user's forearm, and second bar means connected to and extending from each side of said U-shaped forearm cuff means;

a pivot support plate means aligned with said first and second bar means extending from each side of said U-shaped upper arm cuff means and said U-shaped forearm cuff means, each said pivot support plate means including a first pivot screw means, and a second pivot screw means, said first and second bar means on each side being pivotally mounted on said first and second pivot screw means, respectively;

said first and second bar means having intermeshing gear teeth at the pivoted ends on each side of said respective cuff means to ensure controlled pivoting thereof;

a limit guide and support plate means connected to said first and second pivot screw means on the side of said first and second bar means opposite said pivot support plate means to thereby sandwich said first and second bar means between said pivot support plate means and said limit guide and support plate means on each side of said respective cuff means, at least one of said first and second bar means having scale indicia on a surface thereof and a corresponding indicia mark is placed on a pivot plate of said pivot plate means whereby a desired maximum angle of flexion and minimum angle of extension may be identified; and cushion means attached to a surface of said limit guide and support plate means for protection of the elbow of a person when in use;

each said limit guide and support plate means having a first arcuate slot means and a second arcuate slot means, the radial centers of which being located at the corresponding first and second pivot screw means;

upper limit screw means adjustably and lockably located at one end of said first and second arcuate slot means and engageable with upper edges of said first and second bar means on each side of said respective cuff means to limit the maximum flexion of a user's arm to a maximum of 90 degrees; and lower limit screw means adjustably and lockably located in said first and second arcuate slot means and engageable with lower edges of said first and second bar means on each side of said respective cuff means to limit the degree of extension of the forearm of the user relative to the upper arm during the act of throwing; whereby the user is restricted from throwing with the forearm flexed towards the user's ear beyond a maximum flexion angle of 90 degrees, and is further restricted from releasing a ball with an over-extended or fully extended arm, while encouraging the maximum use of the latissimus dorsi muscle to rotate the user's arm during the act of throwing.

3. A throwing arm training device as in claim 2, said upper arm cuff means and said forearm cuff means being formed of plastic material selected from the group consisting of polypropylene, polyethylene, and copolymers thereof.

4. A throwing arm training device as in claim 3, further including a stabilizing screw centrally located on each said pivot support plate means and bearing on said pivot screw means.

* * * * *